(12) United States Patent
Boggs, II et al.

(10) Patent No.: US 11,235,146 B2
(45) Date of Patent: Feb. 1, 2022

(54) APPARATUS AND METHOD FOR TREATING HEADACHES

(71) Applicant: SPR Therapeutics, LLC, Cleveland, OH (US)

(72) Inventors: Joseph W. Boggs, II, Chapel Hill, NC (US); Amorn Wongsarnpigoon, Chapel Hill, NC (US)

(73) Assignee: SPR THERAPEUTICS, INC., Cleveland, OH (US)

( * ) Notice: Subject to any disclaimer, the term of this patent is extended or adjusted under 35 U.S.C. 154(b) by 0 days.

(21) Appl. No.: 15/533,170

(22) PCT Filed: Dec. 10, 2015

(86) PCT No.: PCT/US2015/065108
§ 371 (c)(1),
(2) Date: Jun. 5, 2017

(87) PCT Pub. No.: WO2016/094728
PCT Pub. Date: Jun. 16, 2016

(65) Prior Publication Data
US 2017/0361089 A1 Dec. 21, 2017

Related U.S. Application Data

(60) Provisional application No. 62/090,194, filed on Dec. 10, 2014, provisional application No. 62/113,503, filed on Feb. 8, 2015.

(51) Int. Cl.
*A61N 1/05* (2006.01)
*A61N 1/36* (2006.01)

(52) U.S. Cl.
CPC ....... *A61N 1/0551* (2013.01); *A61N 1/36017* (2013.01); *A61N 1/36057* (2013.01); *A61N 1/36075* (2013.01); *A61N 1/36132* (2013.01)

(58) Field of Classification Search
None
See application file for complete search history.

(56) References Cited

U.S. PATENT DOCUMENTS

| 5,215,086 A | 6/1993 | Terry, Jr. |
| 7,676,271 B2 | 3/2010 | Wahlstrand et al. |
| (Continued) | | |

FOREIGN PATENT DOCUMENTS

| EP | 1935448 | 6/2008 |
| WO | 2013082283 | 6/2013 |

OTHER PUBLICATIONS

Patent Cooperation Treaty (PCT), International Search Report and Written Opinion for Application PCT/US2015/65108 filed Dec. 10, 2015, dated Feb. 25, 2016, International Searching Authority, US.

*Primary Examiner* — Ankit D Tejani
(74) *Attorney, Agent, or Firm* — McDonald Hopkins LLC

(57) ABSTRACT

The present disclosure generally relates to a system for treating headaches and other pain associated with the occipital nerves. More particularly, the disclosure relates to a system of treating pain by selectively activating specific nerve fibers with a single, fault-resistant contact situated proximate to, but not in direct contact with, portions of one or more the occipital nerves. Additional measures ensure the lead does not migrate or fracture, resulting in long-lasting pain relief.

15 Claims, 2 Drawing Sheets

(56) References Cited

U.S. PATENT DOCUMENTS

| | | |
|---|---|---|
| 7,765,012 B2 | 7/2010 | Gerber |
| 8,774,924 B2 | 7/2014 | Weiner |
| 2006/0206165 A1 | 9/2006 | Jaax et al. |
| 2011/0109080 A1 | 9/2011 | Partsch |
| 2012/0310314 A1* | 12/2012 | Bennett .............. A61N 1/36071 607/115 |
| 2013/0158638 A1 | 6/2013 | Zuhlati et al. |
| 2013/0231636 A1 | 9/2013 | Jaax et al. |
| 2014/0128948 A1* | 5/2014 | Clark .................. A61N 1/0558 607/116 |

* cited by examiner

Greater occipital nerve
Lesser occipital nerve
Semispinalis capitis (exposed)

Temporary trial lead

Permanent implantable lead

APPARATUS AND METHOD FOR TREATING HEADACHES

CROSS REFERENCE TO RELATED APPLICATIONS

This application claims priority to International Patent Application No. PCT/US2015/65108 filed on Dec. 10, 2015, which claims priority to U.S. Provisional Patent Application Nos. 62/090,194 and 62/113,503, which were respectively filed on Dec. 10, 2014 and Feb. 8, 2015, all of which are hereby incorporated by reference. Other patent publications identified herein are incorporated by reference as appropriate to the circumstances.

BACKGROUND

The present disclosure generally relates to a system for treating headaches and other pain associated with the occipital nerve. More particularly, the disclosure relates to a system of treating pain by selectively activating specific nerve fibers with a single, fault-resistant lead situated proximate to, but not in direct contact with, portions of one or more of the occipital nerves.

As one example of the magnitude of pain management problems associated with the occipital nerve, headache following traumatic brain injury (TBI) and other traumatic head injuries is a common and severe problem for military personnel as well as the general U.S. population. Approximately 300,000-400,000 of the 1.8 million service members returning from Iraq and Afghanistan have suffered TBI. The most common cause of these injuries is blast exposure, with rates of head and neck injuries as high as 47-59% in some combat units. Also, approximately 1.4-3.8 million individuals in the U.S. general population suffer TBI or traumatic head injury each year, primarily from motor vehicle accidents, falls, and violence Headache is present in up to 90% of mild to moderate TBI patients and results in a low (<32%) return to duty (RTD) rate for military personnel, as well as negatively impact multiple areas of psychological health, including depression symptoms, anxiety, sleep, and cognitive efficiency in the general population. Existing treatments have limited efficacy and/or carry risks of complications, dependence, and debilitating side effects. Case series studies of peripheral nerve stimulation (PNS) of the occipital nerves demonstrate encouraging improvements in pain and quality of life by up to 90%. However, existing devices for PNS are not designed for use in mobile anatomical locations, such as the neck. They are mechanically rigid, have an unacceptably high (up to 66%) rate of complications (e.g., electrode migration and fracture) in these regions.

Individuals with TBI suffer from several psychological health issues (e.g., anxiety, depression, memory/concentration), sensory dysfunction (e.g., blurred vision, light sensitivity, tinnitus, problems with taste/smell), and physical symptoms (e.g., nausea and vomiting, insomnia, fatigue, loss of balance, dizziness), and in particular, headache. Headache is the most common type of pain following TBI, occurring in 50-58% of TBI patients (up to 90% of those with mild TBI). Headaches are moderate/severe in 40-78% of individuals with TBI and other traumatic head injuries and persist ≥1-5 years in 24-50%.

The problems caused by headache and other pain associated with the occipital nerves can negatively impact sleep, depression symptoms, anxiety, and cognitive efficiency, which may already critical issues for these patients. Accordingly, these difficulties can lead to significant disability, impair function, reduce quality of life (QOL), and is commonly associated with depression and post-traumatic stress disorder (PTSD). Pain of this sort can also limit daily activities, as headache severity following traumatic injuries increases due to routine physical activities (63-77% of patients) and is associated with sensitivities to noise (29-40%) and light (33-36%). Due to these many problems, quality of life is poor, and suicidal ideation and attempts are up to 6.5 times more likely for TBI sufferers as compared to the general population.

Existing methods of managing pain from the occipital nerve region, and especially that associated with TBI and post-traumatic headache, are often insufficient. For example Acute pain medications: can provide temporary relief of pain but are not recommended for long-term management of headache, as overuse can lead to medication overuse headache (i.e., rebound headache). Medication overuse headache is reported as occurring in 30-50% of headache patients in tertiary care and headache referral centers.

Non-opioid analgesics (e.g., acetaminophen, non-steroidal anti-inflammatory drugs [NSAIDs]) have relatively minor side effects but are rarely sufficient in managing moderate to severe pain, and chronic use may lead to the development of gastritis or gastrointenstinal bleeding.

Ergotamines and triptans are effective only for certain types of headache. Also, ergotamines can cause nausea when administered orally, and triptans can cause various uncomfortable side effects (e.g., flushing, neck tightness, chest pressure).

Opioids may be effective at relieving pain in some patients but carry the risk of addiction and side effects (i.e., nausea, vomiting, confusion, hallucinations, drowsiness, dizziness, headache, agitation, and insomnia). These side effects may be more severe in patients with TBI and traumatic head injuries. Also, many people do not want opioid medications for fear of addiction.

Prophylactic medications (antidepressants, anticonvulsants, beta-blockers and calcium channel blockers) are used for chronic headache pain. However, they carry risks of side effects (e.g., constipation, weight gain/loss, nausea, fatigue, sedation), and their use is based primarily on anecdotal evidence with few controlled clinical trials to support their efficacy for post-traumatic headache.

Anesthetic nerve blocks may provide temporary relief in a subset of patients. However, repeated injections (every 1-8 weeks, or 2-12 weeks with the addition of corticosteroids) are required to provide relief for chronic headache, and long-term use is not recommended.

Botulinum toxin (onabotulinumtoxinA) injections are FDA approved for treatment of migraines but require repeated treatments (e.g., every 12 weeks) and carry risks of complications (e.g., worsening headache, allergic reactions, neck pain, headache, muscular weakness, eyelid ptosis).

Physical treatments (e.g., physical therapy, acupuncture, massage, heating/cooling of the neck/head) have limited data to support their use and are not commonly used to control severe pain. Physical therapy and exercise may reduce pain and improve performance of activities of daily living, but moderate to severe pain often prevents participation in physical therapy.

Psychological strategies (e.g., biofeedback and psychotherapy) may be used as an adjunct to other therapies, but are seldom sufficient on their own and there are few studies demonstrating their effectiveness.

Pulsed radiofrequency (RF) treatment may be effective for the treatment of some types of chronic headache, but the available evidence is limited. Approximately half of all patients experience the return of their pain after 3-6 months, requiring additional treatment to maintain pain relief.

Surgical procedures (e.g., neurolysis, neurectomy, neuroablative procedures) are performed to treat chronic headache, but evidence supporting these surgeries is limited, and all involve substantial risk. These procedures are irreversible and delayed deafferentation pain often develops after a brief period of pain relief.

Neurostimulation can reduce headache and improve quality of life, but available methods have practical and/or technical limitations.

Non-invasive methods (transcutaneous electrical nerve stimulation; transcranial electrical or magnetic stimulation) cannot deliver continuous therapeutic levels of stimulation to provide reliable pain relief in the majority of patients.

Invasive methods of stimulation (e.g., sphenopalatine ganglion stimulation, vagal nerve stimulation, motor cortex stimulation, spinal cord stimulation, deep brain stimulation) have been used to treat chronic headache pain. However, these methods have weak evidence supporting efficacy that do not warrant the level of invasiveness and risks of surgical complications and side effects.

Thus, present medical treatments of headaches—for example, those following TBI and other traumatic head injuries—are inadequate, and many patients resort to living with pain that is poorly controlled with medications. Additionally, a treatment method to relieve pain associated with the distributions of the greater and/or lesser occipital nerves is needed.

The instances where PNS of the occipital nerves was employed to date have been unsuccessful. These past attempts employed leads designed for spinal cord stimulation, which are placed in the subcutaneous space over and often in direct contact with the occipital nerves in the highly mobile neck joint. Due to lack of lead flexibility and lack of an anchor near the distal stimulating end, these leads frequently migrate and fracture (21-66% of patients). These complications result in loss of efficacy and require additional invasive surgery to remove, reposition, or replace the lead. As an example of the challenges of the prior art, in one study (a randomized controlled trial or RCT), there was approximately one revision surgery for every 3 patients during just the first 3 months of treatment.

Further, these prior art occipital nerve stimulation regimens required leads with multiple electrodes (i.e., contacts) on the lead, resulting in a relatively large apparatus. These previous therapies required numerous electrodes per nerve simply to activate the targeted nerve fibers. However, the multiplicity of points at which the stimulation was delivered often simultaneously activated the non-target nerve fibers in both the occipital nerve(s) and/or outside of the occipital nerves, including other nearby nerves, nerve branches, and other afferent fibers (e.g., cutaneous skin receptors) or efferent fibers. The unintended activation of motor fibes led to unwanted muscle contractions and/or general discomfort for the patient during treatment. Consequently, these systems were complex and uncomfortable for patients.

In addition, the location of previous implantable systems likely contributed to the high rate of adverse events. These systems were placed in the abdomen or upper buttocks in 62% and 100% of patients in the two reported studies. Because leads were tunneled from the occipital nerves down the length of the back/torso, leads were subjected to strain during back and neck movements. Accordingly, patients with systems placed in the abdomen or upper buttocks (N=98) experienced >30% more adverse events.

The bony structures surrounding the occipital nerves, combined with a relative lack of subcutaneous tissue, also present challenges. In particular, the relatively large leads of previous methods are difficult to implement in the head and neck region and, owing to the patient's need to retain mobility in that area, resulted in a high rate of lead migration and/or fracture, both of which limited the efficacy and duration of the treatment.

SUMMARY OF INVENTION

The invention improves upon previously known systems by combining a preliminary verification of the targeted occipital nerves with the use of a lead having only one electrode associated with one nerve. This combination results in a more mobile and failure-resistant therapy.

As used throughout the remainder of this application, the term "occipital nerve" may include the greater, lesser and/or third occipital nerves, singly or in combination, depending upon the context of usage. In the same manner, the term "electrode" will mean the apparatus (including a number of subcomponents, described in more detail below) that is inserted percutaneously into a patients body to deliver electrical stimulation. The "lead" encompasses the electrode but also includes wires and connections to the electrical pulse generator. The wires of the lead that are not directly associated with the electrode are necessarily protected (e.g., by insulating overwraps) to avoid delivering unintended electrical stimulation to non-targeted tissue. The system also encompasses return electrodes and other structure common associated with, and necessary for the proper operation of, neurostimulation.

The invention comprises a method of treating pain associated with the occipital nerve. The method may include any of the following steps:

verifying the pain is associated with regions innervated by at least one of the patient's occipital nerves so as to identify a targeted region of at least one occipital nerve positioning a flexible, coiled neurostimulation lead having a single electrode percutaneously proximate to, but not in direct physical contact with, the targeted region, wherein the electrode comprises a plurality of conductive members, each conductive member being wired in parallel to an electrical stimulation device delivering preliminary therapy for a period of time via the lead while simultaneously preventing migration of the lead, the preliminary therapy comprising pulsed electrical signals sufficient to activate the occipital nerve to provide pain relief without stimulating muscle contractions and sensations of discomfort removing the lead after the patient reports a reduction in pain monitoring the pain reported by the patient subsequent to the preliminary therapy upon a report from the patient of pain that is similar to the preliminary therapy, providing a surgically implanted system comprising a second flexible, coiled neurostimulation lead percutaneously positioned proximate to, but not in direct contact with, the targeted region and a subcutaneous electrical stimulation device located proximate to one of the patient's upper chest, clavicle, skull and neck connecting the second lead to the electrical stimulation device and subcutaneously fixing the electrical stimulation device within the patient delivering long term therapy via the second lead and the pulse generator wherein the electrical stimulation device is attached to the patient's fascia positioning a flexible, coiled neurostimulation lead having a single electrode percutaneously proximate to, but not in direct physical contact with, the targeted region, wherein the electrode comprises a plurality of conductive members surgically implanting a subcutaneous electrical stimulation device proximate to one of the patient's upper chest, clavicle, skull and neck connecting the lead to the electrical stimulation device so that each conductive member is wired in parallel to the electrical stimulation device subcutaneously fixing the electrical stimulation device within the patient delivering neurostimulation therapy via the electrode while simultaneously preventing migration of the lead, the therapy comprising pulsed electrical signals sufficient to sufficient to activate the occipital nerve to provide pain relief without stimulating muscle contractions and sensations of discomfort wherein the electrical stimulation device is attached to the patient's fascia positioning a flexible, coiled neurostimulation lead having a single electrode percutaneously proximate to, but not in direct physical contact with, the occipital nerve, wherein the electrode comprises a plurality of conductive members wired in parallel to an electrical stimulation device delivering therapy for a period of time via the lead while simultaneously preventing migration of the lead, the therapy comprising pulsed electrical signals sufficient to sufficient to activate the occipital nerve to provide pain relief without stimulating muscle contractions and sensations of discomfort wherein the pulsed signals are directionally transmitted only to the targeted region wherein the lead includes shielding to directionally transmit the pulsed signals to the targeted region while simultaneously preventing the pulsed signals from activating non-targeted nerves providing a plurality of leads and positioning each lead so that each lead is operatively associated with a plurality of targeted regions, said plurality of targeted regions in each located in separate occipital nerves wherein the targeted region comprises first and second areas wherein the electrode includes a length of exposed conductive, said length having a first exposed end and a second opposed end with a middle length situated therebetween and further comprising positioning the first exposed end proximate to, but not in direct physical contact with, the first area and the second exposed end proximate to, but not in direct physical contact with, the second area wherein the pulsed signals are adjusted so that appropriate levels of therapeutic current are delivered at the first and second exposed ends while current delivered by the middle length does not innervate muscle contractions and sensations of discomfort wherein the first area is located on a first occipital nerve and the second area is located on a second occipital nerve wherein the lead is substantially parallel to a transverse plane wherein the lead is substantially parallel to at least one of a sagittal plane and a coronal plane wherein the conductive members are arranged to create a plurality of coils in the lead wherein the preventing migration of the lead comprises allowing tissue ingrowth within the lead

BRIEF DESCRIPTION OF THE DRAWINGS

The accompanying drawings illustrate various systems, apparatuses, devices and related methods, in which like reference characters refer to like parts throughout, and in which:

FIG. 1, including

DETAILED DESCRIPTION OF PREFERRED EMBODIMENTS

Figure 1A:
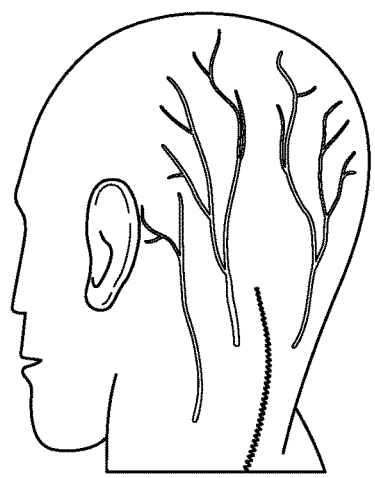
FIGS. 1a and 1b, illustrates the location of treatment according to an embodiment of the invention.

Peripheral nerve stimulation (PNS) of the occipital nerves is a promising non-pharmacological (non-opioid) therapy. The present teaches the use of a durable, flexible, coiled leads with fault-resistant redundancies within the electrode. After verifying the targeted nerve fibers, the single electrode within the lead is positioned proximate to, but not in direct contact with, the occipital nerve(s) to overcome challenges from previous treatment methods. This system and method may be used for other types of severe and disabling pain.

In particular, the inventive therapy will fulfill the unmet need, especially for a treatment that relieves headaches following TBI and other traumatic head injuries, as well as other pain associated with the occipital nerves. This approach delivers PNS to the occipital nerves and overcomes the challenges of lead migration and lead fracture during use that limit existing approaches to PNS.

PNS of the occipital nerves can be effective in treating headache, particularly when the region of pain is in the distribution of the occipital nerves. PNS of the occipital nerve reduced pain by 40-90%, decreased the frequency of headache days by 50-80%, and improved quality of life by 70-90%. A majority of patients with headaches (up to 51-80%) following TBI and other traumatic head injuries report pain in regions innervated by occipital nerves, and PNS has demonstrated effectiveness in treating headache from a variety of causes including trauma, as documented in multiple studies in over 300 patients. In particular, PNS of the occipital nerve can reduce pain and improve Quality of Life ("QOL") both by an average of >70% when the region of worst pain is innervated by the occipital nerve. Also, refining the patient population to those with pain within the distribution of specific peripheral (e.g., occipital) nerves in the head may increase the success rate, and good to excellent pain relief was achieved in over 80% (n=50) of patients at 2 years follow up.

The present teachings may employ comparative blocks to optimize patient selection and to verify the targeted region of the occipital nerve(s) that must be innervated for pain relief. Variability may be reduced by using comparative blocks, where the effect of an anesthetic block is compared to the effect of one or more subsequent blocks with a different anesthetic agent or saline (placebo) to rule out potential placebo-responders. When pain is confirmed to be in the distribution of the peripheral nerve receiving stimulation (e.g., occipital nerve), successful pain relief can be achieved in over 80% of patients. This verification may also be accomplished by way of an electrode delivered via a needle probe, via the inventive lead described below or other means of testing and, preferably, comparing pain response to definitively identify the targeted area.

Additionally, in a preferred embodiment, patients may receive stimulation (e.g., for >1 day or more preferably 7-14 days) prior to using a fully implantable system. In a non-limiting example, stimulation prior to using the fully implantable system may be provided for a longer duration than has been described in the prior art (e.g., 30-60 days), which may decrease the false-positive rate of the trial and increase the chance that patients that are implanted with the implantable system will have successful pain relief (i.e., minimizes the chance that patients will be implanted with the system but ultimately have poor pain relief). In another non-limiting example, stimulation may be delivered for shorter periods of time (e.g., 7-14 days) to provide comparable trials as in the prior art but with lower incidents of device failures due to the unique features of the invention. Further, it may be preferred to screen and exclude patients who have been overusing medications, so as to reduce the chance of confounding results from medication overuse headache (i.e., rebound headache).

In one embodiment, patients may test the therapy at home using a temporary system, composed of the percutaneous coiled migration-resistant lead connected to an external pulse generator. If the in-clinic test stimulation and home trial are successful, the temporary system may be replaced with a fully implanted system, composed of an implantable coiled migration-resistant lead connected to a pulse generators (IPG), and preferably one that is implantable, rechargeable and/or miniaturized.

The invention enables selective and/or preferential activation of target nerve fibers in the occipital nerve(s) while avoiding unwanted muscle contractions, sensations of pain/discomfort and/or activation of non-target nerve fibers (whether in the occipital nerves or otherwise). This successful activation is achieved by placing self-anchoring leads (e.g., with distal anchoring mechanism or with a shape permitting tissue ingrowth) within electrical proximity to the occipital nerve (innervating the region of pain) but not in direct physical contact with the occipital nerve (i.e., the electrode is placed to stimulate the target fibers selectively without physically touching the occipital nerve). The optimal distance between the electrode on the lead and targeted region of the nerve is usually a matter of millimeters, with ranges bounded between 0.1 and 50 millimeters being preferred. Ultimately, the distance will depend upon the strength of the pulsed signals used for therapy and the conductivity/impedance of the patient's tissue in the targeted area, and the verification step will customize the parameters to the needs of each patient.

Significantly, the selective/preferential activation of target fibers in occipital nerves is achieved while avoiding activation of non-target fibers through the use of a single electrode spaced away from but proximate to the nerve(s), as described in greater detail below. By way of example rather than limitation, reference is made to United States Patent Publication 2012/0290055. Ultimately, the goal is stimulate type Ia and Ib nerve fibers within the occipital nerve(s). Type III and type IV fibers will not be targeted.

While there is debate as to whether the occipital nerve includes motor fibers, it will be understood that the inventive method's emphasis on maintaining a distance between the nerve and the electrode gives rise to the possibility of unwanted stimulation of surrounding nerve branches and/or bundles. Therefore, proper verification and targeting must avoid cutaneous afferent and/or motor fibers so as to eliminate unwanted muscle contractions and/or sensations of discomfort for the patient.

The lead is flexible, self-anchoring, migration resistant, fracture resistant, multi-fault tolerant, and infection resistant. The flexible coiled leads are designed specifically for PNS to reduce migration and fracture. Both the temporary percutaneous lead and fully implantable lead have a coiled structure, allowing the lead to flex and bend when subjected to forces rather than migrate or fracture. There may be one or more coils, with the coils composed of bundles of conductive wires. Each of the conductive wires, as well as the coils, are wired in parallel to the electrical stimulation/pulse generator to ensure that a fracture sustained in a single wire does not inhibit therapeutic pulses delivered by the lead as a whole. The interstices of the coils will allow tissue ingrowth to better secure the lead within the patient's body, thereby reducing lead migration.

Also, the leads may have anchors at their terminal stimulating ends to secure the lead in the tissue, increasing resistance to lead migration. These anchors are designed to flex avoid damaging tissue during removal. To the extent distal or other anchors are provided on the lead, additional migration protection can be realized.

The migration-resistant leads have been placed in and near mobile anatomical structures (e.g., joints in the arms, legs, and torso) and have been proven effective for peripheral nerve stimulation and generating comfortable sensations covering the regions of pain to relieve chronic pain.

Figure 2:
FIG. 2 illustrates exemplary leads that may be used in an embodiment of the invention.
Figure 2:
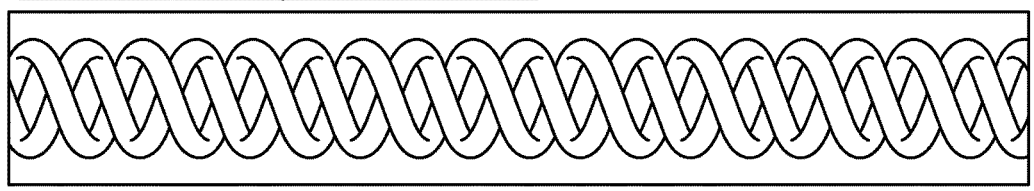

The temporary lead used during the stimulation trial (preliminary treatment) is a single, helical coil wound from a multiple-strand stainless steel wire (FIG. 2, which shows a seven-strand wire). The plurality of strands in the wire core of the lead is independently connected to the IPG and gives rise to its multi-fault tolerant traits. Specifically, the multiplicity of wires/strands enables the lead to continue to function and deliver therapy reliably via a single point of contact proximate to the nerve(s) even if a potential fracture (i.e., fault) occurs in one or more of the conductive wires or strands of wires. For example, because the conductors are wired (connected) in parallel to the same pulse generator, one or more can break and yet the system as a whole can continue to function as designed, continuing to provide pain relief to the patient. Previously, multi-fault tolerant leads for delivering electrical stimulation were believed to be impractical, especially insofar as the increased diameter caused by multiple wires and the need for multiple leads made it prohibitive to use in the head and neck region targeted by this invention (e.g., there was not enough anatomical space between bony or other structures and the skin).

The helical or open-coil structure of the lead is also desirable. The open-coil design allows tissue ingrowth between the coils, which secures the lead along its entire length beneath the skin. In over 250 leads used for 2-7 weeks for the treatment of pain, there have been no reported lead migrations or fractures during use. Additionally, tissue ingrowth will impede infectious agents.

The coiled implantable lead (FIG. 2) may also be used for long-term pain relief (Stage 2) in patients who achieve significant pain relief in Stage 1, as described below. It should be noted that Stage 1 and Stage 2 are independent embodiments, and the effects of the invention may still be enjoyed even if only one or the other embodiment is utilized.

The unique double-coiled design for the lead was optimized and bench-tested for great flexibility, safe tissue response, and mechanical endurance in high stress environments. The use of two or more coils within the lead enables the lead to sustain multiple local failures along the length of the lead (either in the strands of wire comprising the coils or even in the entirety of one of the coils) while continuing to deliver effective therapy because the wires and the coils are electrically coupled to the same stimulation source (e.g., IPG). Stimulation thresholds remained stable for 100% of the 81 leads that were tested over a 2 year period, demonstrating that the implantable lead resisted migration and fracture. Further, the implantable coiled leads have a >98% probability of resisting fracture and remaining functional after 16 years of use, whereas the conventional leads used in the previous randomized controlled trials of PNS of the occipital nerves had a comparable survival rate over a period of only 3 months. The exceedingly low rates of fracture and migration of the inventive lead are expected to result in lower rates of lead revision, replacement, and removal, and thus higher rates of long-term success and safety.

The percutaneous lead reduces the risk of infection by limiting both pistoning and the size of the exit site through the skin. The coiled design reduces pistoning by allowing the lead to stretch and compress, minimizing movements in or out of the skin (FIG. 2). The diameter of the coiled lead (0.2 mm) is smaller than the conventional leads used for PNS of the occipital nerves (approximately 1.3 mm), producing a smaller exit site, and thus, a smaller entry point for pathogens. In >1000 leads left indwelling for up to 30 days (more than twice as long as the two weeks proposed for this study), the infection rate was <0.1%. This is significantly lower than the rate for conventional leads used in existing methods of PNS by more than an order of magnitude (30 day rate=1.6%). As a result, the use of the percutaneous lead for the treatment of headache for 2 weeks is expected to have minimal risk of infection and significantly lower risk than existing stimulation therapies.

A single electrode is provided on the lead, preferably near its distal end (i.e., closest to the patient's body). The electrode comprises an exposed section of the coils/wires. Additional shielding may be provided to allow the pulsed signals delivered by the electrode to be directionally transmitted toward a desired portion of the body and away from the surface of the skin and towards the nerves. In practice, the electrode portion of the lead necessarily comprises two exposed ends, with a middle section disposed between the ends.

Figure 3:
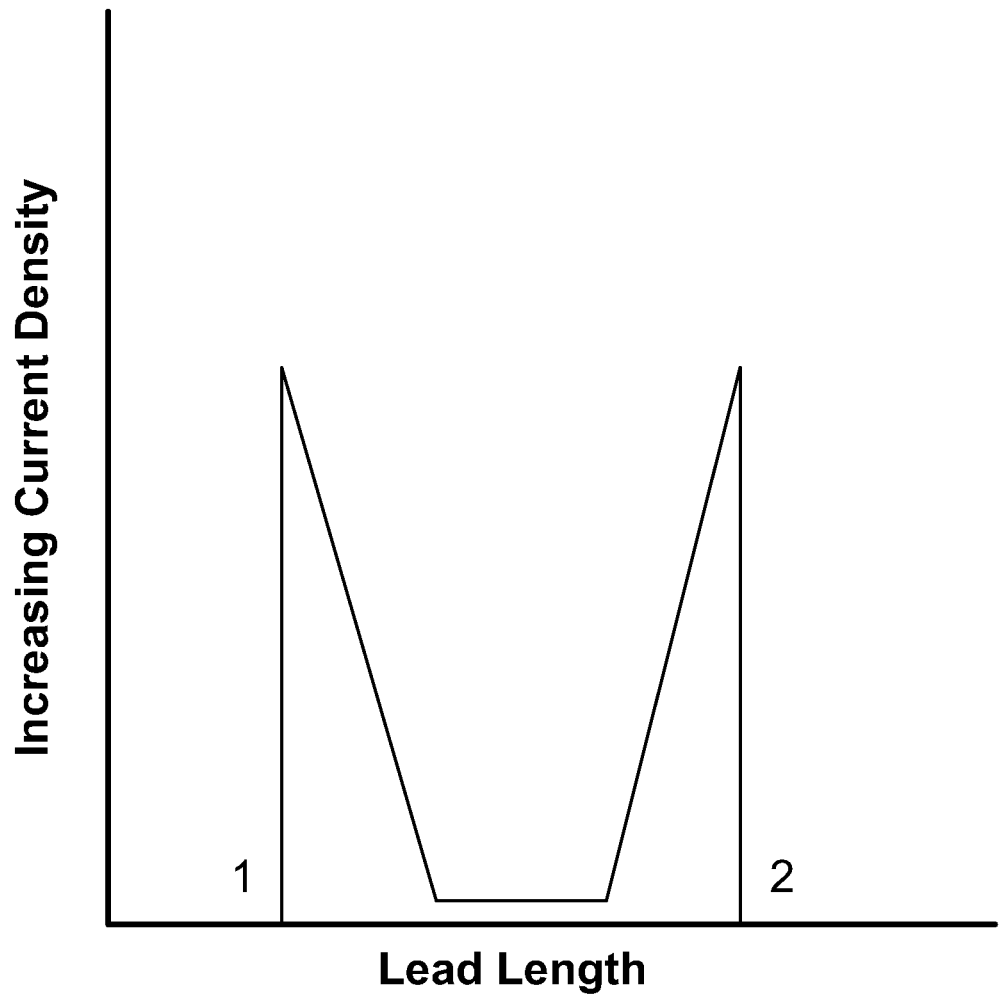
FIG. 3 illustrates an exemplary profile of the current density delivered along the exposed length of an electrode according to an embodiment of the invention.

The inventors have discovered, when current is delivered to the lead, the pulses generated by the electrode (and delivered as therapeutic signals to the patient) tend to have their greatest current density at the two exposed ends. In contrast, the middle section tends to have significantly reduced current. This phenomenon is illustrated in FIG. 3, with reference numerals 1 and 2 representing the exposed ends of the electrode. FIG. 3 is merely exemplary, although it should be noted that the axis labeled "length of the lead" demonstrates that the electrode need not be positioned at the terminal end of the lead. Indeed, to the extent additional anchoring mechanisms are used, it may be necessary for the electrode to positioned proximal to the anchor structure.

In any event, by positioning the terminal ends of the electrode, the treatment can be delivered with a single electrode. This approach enables a smaller lead and allows for more versatility in terms of its placement, particularly in view of the mobility patients expect and need to retain in order to conduct daily activities. Notably, the length of the exposed portion of electrode may be adjusted to better coincide with the targeted area or areas of the occipital nerve.

Multiple leads having the construction described above may also be used. However, in this case, only one lead and one electrode is required to target one or more of the nerves. In this manner, the overall size of the system required to deliver the therapy is once again minimized.

The leads may be placed be placed in the transverse plane, or parallel to at least one of the sagittal and coronal planes, depending upon the findings established during the verification step. As above, this may enable treatment of multiple locations and/or multiple occipital nerves by only one lead.

For purposes of this invention, the transverse plane (also called the horizontal plane, or transaxial plane) is an imaginary plane that divides the patient's body into superior and inferior parts. The sagittal plane is an imaginary plane parallel to the sagittal suture so as to divide the patient's body into left and right. The coronal plane (or frontal plane) divides the body into dorsal and ventral (e.g., back and front or posterior and anterior) portions. In a non-limiting example, leads may be placed intramuscularly near the occipital nerves. This may increase the stability of the lead (e.g., increasing resistance to migration) and allow the lead to be placed farther from cutaneous fibers to avoid cutaneous discomfort. In another non-limiting example, stimulation parameters may be delivered such that the activation of motor fibers may be avoided (e.g., through use of low pulse durations). Placing leads deeper (i.e., farther away from the skin surface) minimizes skin erosion, as can occur with larger more rigid leads (e.g., spinal cord stimulation leads). In a non-limiting example, the intramuscular placement may be at a level before or after nerves emerge from muscles (e.g., in the neck) and become superficial (i.e., subcutaneous). In another non-limiting example, leads could be placed intramuscularly closer to nerve roots to stimulate more than one occipital nerve (e.g., greater, lesser, third) simultaneously. In another non-limiting example, intramuscular placement of the lead may enable the insertion of the lead below the hairline in the back of the head, which does not require the hair to be shaved or removed for insertion.

The stimulator for Stage 1 may include a "sham" mode, which may be identical to normal modes from the perspective of the patient, but no stimulation is delivered. Alternatively, stimulation with untherapeutic parameters (e.g., very low amplitude, pulse duration, or duty cycle). This sham mode may be used to screen patients and/or to better verify the precise location and efficacy of treatment delivered according to this method.

The IPG may be smaller and thinner than existing IPGs, which allows the IPG to be placed discreetly in the upper chest, preferably below the clavicle. Alternatively, IPG could be placed in head or neck. A pocket may be made in the skull to house the IPG to reduce the profile. Placing the IPG in the upper chest is expected to reduce lead migration compared to placing the IPG in the lower back, where frequent back and neck movements can pull on the lead and cause migration from its original location. Also, the small size and slim profile of the IPG are expected to reduce cosmetic concerns (i.e., visible bump from IPG protruding through the skin). Further, both the size of the IPG and lead is such that tissue erosion will be mitigating substantially in comparison to previously used systems.

The invention may employ established screening methods to reduce the variability in patient response. Comparative (placebo-controlled) block of the occipital nerves will verify that the patient's pain is located primarily in the regions innervated by the occipital nerves, which has high specificity (88%) and improves the chance of success with PNS. The comparative block may contrast the effects of actual (lidocaine) injections and placebo (saline) injections on separate days; patients must obtain substantial pain relief from the actual injections and a limited/no response to the sham injection to rule out a placebo response. Additionally or alternatively, all patients may receive active stimulation during lead positioning and/or a preliminary trial (i.e., Stage 1), preferably for a minimum of 1-2 weeks. The preliminary trial is expected to reduce the variability of patients who may otherwise proceed to a fully implantable system in long-term treatment. In addition, patient variability will be reduced further by excluding individuals overusing acute pain medications. Collectively, these steps may further optimize the probability of obtaining pain relief.

Using comfortable sensations in the regions of pain during preliminary stimulation may provide an even higher degree of specificity and sensitivity. If the comfortable sensations cover the region of pain, the patient will likely notice a reduction in pain over the course of the therapy.

In clinical practice, the ability to maximize pain relief is often limited by unwanted muscle contraction and/or discomfort. Previous approaches to PNS of the occipital nerves employed long pulse durations (90-450 μs) and suffered from high rates of intolerable muscle contractions. The present method of PNS utilizes selective stimulation (e.g., short pulse durations of 15-20 μs of 30 mA delivered at 100 Hz) to generate comfortable sensations while avoiding discomfort and muscle contractions. Additional ranges for pulse durations include 0-500 μs at 0-50 mA and, preferably 20-200 Hertz, although any whole integer within these stated ranges may form the lower and/or upper limit for certain aspects of the invention. In addition, the inventors have found that frequencies in excess of 1,000 Hertz may be useful in blocking nerve conduction of pain signals, thereby delivering pain relief.

The present teachings may comprise a 2-stage peripheral nerve stimulation (PNS) system to relieve chronic headache and/or neck pain in individuals with or without traumatic brain injury (TBI) and other traumatic head injuries resulting in headache. To qualify for the fully implantable system in long-term treatment (i.e., Stage 2), it may be desirable for patients to obtain some degree of pain relief (e.g., ≥50%) in preliminary treatment (i.e., Stage 1) during active stimulation compared to baseline.

Stage 1:

To the extent it is used, the procedures for Stage 1 may include any combination of the following: Screening, Baseline, Lead Placement Testing, Home Use, and Follow-up.

Screening: Adults who have suffered traumatic brain injury (TBI) or other head injury resulting in chronic headache or who otherwise experience head or neck pain associated with the occipital nerve(s) are prime candidates.

Patients may be screened using double-blinded ultrasound-guided comparative block of the greater occipital nerves to confirm that their pain is in the regions innervated by the nerves. Ultrasound-guided injections may be applied to the greater occipital nerves using standard procedures. Ultrasound guidance enables more specific targeting of the greater occipital nerves and reduces the chance of false-positive responses from block of other nerves. For example, patients may receive either actual block or sham block at one time point, and receive the other block at another time point. The order of presentation can be randomized, and both the patient and evaluator can be blinded to further improve efficacy.

Actual blocks may consist of 2.5 cc of 1% lidocaine, and the sham injection may include 2.5 cc of saline. The half-life of lidocaine is 1.5-2 hours, and the effects of the block will have dissipated sufficiently by the subsequent visit (>24 hours later). Alternatively, neurostimulation or other methods may be used in this step.

To qualify and continue with the treatment, it may be desirable for the screening to produce some (e.g., >50%) reduction in pain lasting for some duration (e.g., at least 20 minutes) to demonstrate that the patient's pain is localized to the regions innervated by the occipital nerves. Also, it may be desirable for any placebo (sham) injection not to produce pain reduction (e.g., greater than 30%) to confirm that that the responses observed with the actual injections were not due to a placebo response. In addition to confirming that the region of pain is innervated by the targeted occipital nerves, this comparative placebo-controlled block may also reduce the proportion of placebo responders who may not otherwise sustain long term benefits according to this invention.

Baseline: After qualifying, patients may record outcome measures, such as pain, medication usage and pain characteristics (headache duration, and frequency) for a period of time, preferably at least one week. The record should be started at least 24 hours after screening to ensure that the effects of the comparative block have completely disappeared.

Lead Placement Testing: Patients will be prepared for the outpatient lead placement procedure. Hair on the back of the head may be removed, cleansed, and draped using aseptic technique. Alternatively, the hair may remain and the lead may be inserted below the hairline and directed towards the occipital nerve (e.g., superiorly, towards the top of the head). Local anesthesia may be administered at the insertion site prior to lead implantation. If necessary, intravenous (IV) conscious sedation may be administered prior to lead placement. Lead placement may be guided using imaging, such as ultrasound imaging and/or fluoroscopy or any other appropriate method.

Leads will be placed to target the occipital nerves (FIG. 1b) and/or as further determined by the screening. If the patient's pain is unilateral as described by the patient and confirmed via the nerve blocks used during screening, then only one lead would be placed to target the appropriate occipital nerve. Otherwise, leads will be placed to target the occipital nerves on each side of the head. It is expected that most patients will require bilateral stimulation, as 60-90% of headaches following trauma are bilateral.

Figure 1B:
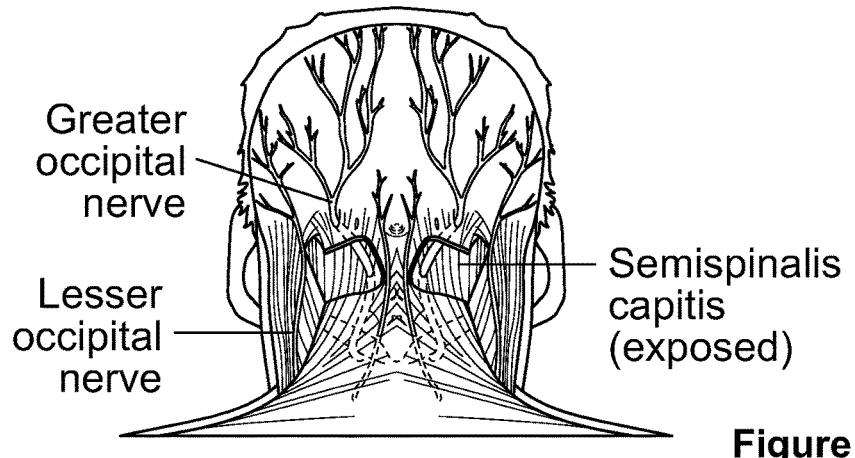

The leads may preferably be directed superiorly parallel and medial to the nerve to avoid the occipital artery, which runs parallel and lateral to the nerve. The target location may be the subcutaneous space near where the greater occipital nerve (on each side) emerges from the semispinalis capitis muscle, approximately 20-30 mm inferior (range: 16-36 mm) to the external occipital protuberance (EOP) and 11-15 mm lateral (max: 28 mm) to midline (FIG. 1b). Test Needles may be used prior to placement of the temporary percutaneous lead. The Test Needle may be advanced and retracted until the optimal location is determined to guide the subsequent placement of the percutaneous leads. The percutaneous leads may be placed within tissue proximal to the nerves (preferably, approximately 0.5 cm away from nerve). In all cases, the lead need not come into direct contact with the nerve.

During Lead Placement, test stimulation may be used to provide comfortable sensations to the regions of pain, verifying that electrode placement and stimulus intensity are sufficient to activate the target nerve and provide pain relief.

The leads may be used to deliver biphasic current-regulated stimulation pulses to maximize patient comfort and pain relief as described in our team's previous studies. Stimulation will be delivered using safe (non-damaging, <0.4 $\mu C/mm^2$) stimulation parameters, including short (15-20 µsec) pulse duration and a frequency of 100 Hz. Stimulation amplitude will be adjusted to maximize pain relief (≤20 mA). These are the ideal settings to decrease pain by stimulating comfortable sensations that overlap with the regions of pain without causing unwanted muscle contractions or cutaneous discomfort. In a non-limiting example, patients may control the stimulation parameters themselves and may adjust as needed (e.g., changing parameters and/or increasing intensity upon onset of headache). In another non-limiting example, the stimulation parameters may adjust automatically (e.g., different parameters may be used at different times of day or month; different parameters may be used in different temperatures, weather conditions, or environments to prevent headaches induced by these conditions), and stimulation parameters may be adjusted based on closed-loop feedback (e.g., sensor detects headache or onset of headache and adjusts parameters automatically to provide pain relief or prevent headache).

During lead placement, if pain is present in the regions innervated by the lesser and/or third occipital nerves, then these nerves may be targeted as an additional or alternative treatment approach. These leads would be placed to target the lesser/third occipital nerve(s) using a similar approach as with the greater occipital nerves. Imaging guidance will be used to identify the location where the lesser occipital nerve emerges from the sternocleidomastoid muscle and becomes superficial. Preferably, the location is approximately 70 mm (range: 30-90 mm) from midline and 55 mm (range: 30-80 mm) inferior to the line connecting the left and right external auditory canals. Leads will be placed inferior to this location in the tissues surrounding the nerve, and lead location and stimulation parameters will be adjusted as described previously to obtain maximal coverage of the regions of pain with comfortable sensations without generating muscle contractions.

Home Use: Patients will use the preliminary system without the need for supervised care. The optimal period for this preliminary trial (i.e., Stage 1) is 7-14 days, with the option of including a placebo treatment to verify efficacy. Each percutaneous lead will be connected to an external stimulator, and all patients will use the system. Significantly, because of the mobile nature of the system and resistance to negative sequelae of movements, the patient should be able to continue with daily activities.

Stimulation may be delivered continuously for up to 24 hours a day. In another non-limiting example, stimulation may be delivered for a set number of hours per day (e.g., 6 hours per day). In another non-limiting example, stimulation is delivered as needed (e.g., only when experiencing a headache; when the patient experiences a migraine aura). Stimulation may be used to treat a headache in progress and/or to prevent headaches (e.g., prophylactically). In another non-limiting example, stimulation may be delivered using non-continuous trains of pulses (e.g., duty cycle), and the pulses may be delivered via regular or irregular patterns. Patients may record medication usage and headache intensity, duration, and frequency (e.g., in a diary).

After lead placement (e.g., after 7 days), patients will return to the clinic to determine if active stimulation produced pain relief. The stimulus parameters may also be adjusted to obtain comfortable sensations in the appropriate target areas and/or to make adjustments as necessary in response to a placebo/sham treatment regimen. Additional visits to verify and better accomplish these aims may be employed prior to moving on to Stage 2.

Lead Removal: Patients may return at a subsequent point. Leads can be removed using gentle traction during a brief (<5 minute) outpatient procedure. The insulating portion of the percutaneous lead may be composed of a non-stick material (e.g., PFA, Teflon), and the lead may be designed to straighten out to facilitate removal when steady gentle traction is applied. Generally speaking, lead removal is not uncomfortable and should not require pain medications or anesthetics. To the extent that the inventive method has been shown to deliver long-term (i.e., at least 3 months pain-free) pain relief, some patients may have the leads removed without the need for additional treatment and/or surgical intervention.

Follow-up: Patients may return after the end of trial stimulation for a safety evaluation of the lead exit site, as well as less regular (e.g., monthly) monitoring to measure the time course for return of pain, preferably for at least 3 months. Patients who did not experience reduction (e.g., ≥50%) in pain during the active stimulation period may not derive benefits from Stage 2.

Stage 2:

Patients must have responded to stimulation during screening and/or reported highly clinically significant pain relief (>50%) during the active portion (stimulation on) of Stage 1. Responders that have a return of pain within 3-6 months of the end of Stage 1 may receive an implantable lead connected to an implantable pulse generators (IPGs). The system may be installed by a physician in a short (~1 hour) outpatient procedure or during an inpatient procedure. The procedures for Stage 2 are classified according to the following time periods: Surgery, Evaluation, and Follow-up.

Surgery: Patients receive a fully implantable system in Stage 2, and in a non-limiting example, patient may wait until their pain returns to within a percentage (e.g., 30%, 40% or 50%) of their baseline score and/or with a minimum level of pain (e.g., ≥4 out of 10). It has been determined that a few weeks of stimulation may produce several months of pain relief, so it is desirable to confirm that pain has returned to baseline prior to proceeding to the fully implantable system.

Prior to beginning Stage 2, patient eligibility may be re-verified, preferably via the screening process described above. The implantable system may be placed during an outpatient procedure. The procedure to place the implantable leads is similar to the procedure for placing the percutaneous leads, with the exception that it may be done in an operating room with the use of monitored anesthesia care (MAC) or general anesthesia (after Test Stimulation, during lead tunneling and IPG placement). Test Needles (as in Stage 1 Lead Placement Testing) may be used to confirm the optimal placement of the leads. A small incision may be made to insert an Introducer (a custom-tapered needle probe preloaded inside a commercially available sheath) at the optimal location determined for the first lead. Test stimulation may be delivered via the Introducer needle as the Introducer is advanced to determine the optimal location to maximize coverage of the regions of pain with comfortable sensations.

When the Introducer is in the desired location, the needle probe will be removed and the lead will be inserted into the sheath. Test stimulation will be applied to confirm proper placement. Once lead placement is confirmed, the sheath will be withdrawn, leaving the lead anchored in place. Stimulation will again be applied to the lead to ensure that the lead did not move during removal of the sheath. This procedure will be repeated for an additional lead to target the other occipital nerve(s) if necessary.

A location for the implantable IPG subcutaneous pocket will be identified such that it is positioned in the chest just below the clavicle, or possibly in the skull, neck or upper chest. Placing the IPG in the upper chest is expected to reduce lead migration compared to placing the IPG in the lower back, where frequent back and neck movements can place strain on the lead and cause migration from its original location. In addition, the IPG may be small in size and have a slimmer profile relative to existing IPGs, which is expected to reduce cosmetic concerns (i.e., visible bump above IPG). An incision will be made and the subcutaneous IPG pocket will be created. A strain relief loop in the lead near the distal end may be created, and a tunneler may be inserted into the implant pocket and directed subcutaneously toward the lead incision sites. The proximal end of the lead will be inserted into the IPG receptacle and the set-screw will be tightened to secure the connection. The IPG will be placed in the pocket, and the remaining slack of the lead will be coiled to create a second strain relief loop and inserted under the IPG (between the IPG and fascia covering the underlying tissue). The IPG will be sutured to the fascia using non-absorbable suture through the suture hole in the header.

Stimulation will then be turned on and parameters will be adjusted to obtain maximum pain relief as in Stage 1.

It is anticipated that the implantable systems will remain in place indefinitely and continue to function and provide pain relief.

In addition to reducing headache intensity, the invention may reduce duration of headache episodes and/or headache days (i.e., days during which the patient suffers a headache of moderate to severe intensity for ≥4 hours). The invention is expected to reduce the duration of headache episodes as well as the frequency of headache days. The invention may reduce medication usage (including opioids [narcotics] and non-opioid [non-narcotic] analgesics) instead of or in addition to reductions in headache intensity.

The invention is expected to reduce headache pain, resulting in improvements in headache-related disability. The invention may also reduce depression (e.g., by providing pain relief). For patients with traumatic brain, head, or neck injuries, the invention may improve related symptoms (e.g., cognitive function, psychological health outcomes).

The therapy is expected to provide continuous, all-day pain relief. Based on previous studies, reductions in pain are expected to be immediate upon the start of treatment and continue as long as treatment is delivered. Furthermore, the improvements in pain are anticipated to reduce pain's interference with daily activities, resulting in improved quality of life as participants are able to resume their normal lives.

It will be understood that the methods and apparatus appropriate for Stage 1 may be utilized in Stage 2, and vice versa. Further, as noted above, the method may include Stage 1 as a precursor to Stage 2, or the individual Stages may be performed independently to obtain the benefits of this invention.

Pain frequency and intensity (and combinations thereof) are useful metrics to judge pain relief according to the invention. To that end, known protocols and procedures may be used, including but not limited to:

Headache pain intensity may be measured using ratings of average pain in the last 24 hours on a 0-10 numerical rating scale, where zero indicates "no pain" and 10 indicates "pain as bad as you can imagine" (Brief Pain Inventory, Short Form). The BPI-SF is a widely used assessment designed to measure pain intensity and the interference of pain on daily activities and moods. In addition, the BPI-SF has been used in many chronic pain studies, including studies evaluating peripheral nerve stimulation.

The Mayo-Portland Adaptability Inventory (MPAI-4) may be administered. The MPAI-4 is a reliable and validated set of 30 items assessed in 3 subscales: Ability Index (physical and cognitive abilities), Adjustment Index (emotional and behavioral self-regulation, interpersonal activities), and Participation Index (community integration). Each item is rated on a 5-point scale (0-4) for a total raw score of 115 points, which is converted into a T-score that is normalized to a reference group (0-100, mean=50, standard deviation=10).

Analgesic use is recommended as one of the core outcome domains in chronic pain studies. Information on analgesic usage may provide additional indication of the effectiveness of the treatment under evaluation when combined with the primary outcome measure (pain intensity).

The Headache Impact Test (HIT-6) may determine the effect of headache on social functioning, role functioning, vitality, cognitive functioning and psychological distress. The HIT-6 consists of 6 items and is a validated, reliable, and common measure of headache-related disability, including in patients with headache following TBI and other traumatic head injuries.

Change in physical functioning and the impact of pain on activities of daily living (ADL) will be measured using the Pain Disability Index (PDI), a seven-question survey that asks the subject to rate the level of disability they experience related to family/home responsibilities, recreation, social activity, occupation, sexual behavior, self-care, and life-supporting activity on a scale of 0 to 10, where 0 is "no disability" and 10 is "worst disability". The PDI is a simple and rapid tool for evaluating the impact of pain on physical functioning with established reliability and validity.

The Beck Depression Inventory Version II (BDI-II) is used frequently in both clinical assessment and research. In the present study, it will be used to assess the level of depressed mood before, during, and after treatment. The BDI-II is recommended as one of the core outcome measures in chronic pain studies to assess emotional functioning, and has been used in multiple chronic pain studies with established validity and reliability in assessing symptoms of emotional distress and depression. Chronic pain is a complex, multidimensional phenomenon with both sensory and emotional aspects, making it important to measure depression in pain treatment studies.

The reliable and validated Trail Making Test (TMT) is recommended as a key measure of cognitive outcomes. The widely-used TMT measures attention, speed, and mental flexibility and will be administered to assess changes in cognitive function over the course of the study. The TMT consists of 2 parts, both of which measure the time required for patients to draw lines connecting 25 circles containing numbers and letters in a specified order on a piece of paper.

The Patient Global Impression of Change (PGIC) scale will be administered to assess patient perception of overall improvement. The PGIC scale rates improvement with treatment on a seven-point scale that ranges from "very much worse" to "very much improved", allowing patients to combine all of the components of their experience into one overall measure and allowing clinicians to assess the clinical significance of improvement or worsening over the course of the study. The measure has been frequently used in chronic pain studies and the data have provided a responsive and readily interpretable measure of patients' assessments of the clinical importance of change due to treatment relieves headache, resulting in improved times on the TMT that reflect improved cognitive function.

EXAMPLE

This study demonstrated that the proposed approach can stimulate nerve trunks comfortably without causing muscle contractions and provide immediate and sustained reductions in pain following traumatic injuries, such as lower-limb amputation. Coiled migration-resistant percutaneous leads were placed in the upper thigh/buttocks under ultrasound guidance to within 0.5-3 cm of the femoral and/or sciatic nerves (i.e., a single lead per nerve) within the tissue surrounding the nerves, and stimulation was delivered using an external pulse generator. Comfortable sensations covering the regions of pain were obtained without muscle contractions in 14/16 patients with no complications during lead placement. In the 14 patients that experienced comfortable sensations, "Pain Right Now" (Question 6 of Brief Pain Inventory Short Form) was reduced by an average of ≥75% compared to before stimulation, and all 14 experienced highly clinically significant pain relief (≥50%).

Pain relief was sustained in the home environment during the 2 week trial. Nine patients continued with treatment after the in-office test, and reductions in pain were sustained during the 2-wk treatment. Patients rated pain at baseline and at end of treatment using the BPI5 (i.e., average daily pain). All patients reported clinically significant (≥30%) reduction in pain at 1 week and at end of treatment (average reduction=76%) (FIG. a.8.*a*). Also, 6 of 9 patients (67%) reported highly clinically significant (≥50%) reduction in pain at 1 week and end of treatment. Analgesic usage decreased (n=3) or did not change substantially (n=6) during the study, indicating that pain reductions were not due to increased analgesic usage.

The approach provided herein improved quality of life and reduced pain interference, pain disability, and depression. The interference of pain with daily activities (general activity, mood, walking ability, normal work, social relations, sleep, and enjoyment of life) was assessed using question 9 of the Brief Pain Inventory-Short Form. On average, the 9 patients in the home trial reported an 82% reduction in the interference of pain on daily activities, including 4 (44%) patients who reported no pain interference in all seven domains at the end of the stimulation period. Also, the 9 patients reported a 73% mean decrease in disability due to pain as measured by the Pain Disability Index (PDI), a survey that measures the degree to which pain disrupts activities such as work and athletics. In addition, patients reported a 47% mean reduction in depressive symptoms per the Beck Depression Inventory (BDI-II). All patients reported their quality of life to be either "minimally improved" (n=1) "much improved" (n=5) or "very much improved" (n=3) at the end of stimulation compared to baseline (Patient Global Impression of Change survey).

Improvements in pain, pain interference, and pain disability remained clinically significant after EOT. Patients continued to experience an average of >40% pain relief, reductions in pain interference of 55%, and 67% reduction in pain disability 4 weeks after EOT, indicating that the benefits produced by our approach to peripheral nerve stimulation enabled participants to resume daily activities and improved their quality of life, all without experiencing failure or migration of the lead.

The invention claimed is:

1. A method for treating pain in a patient, the method comprising:
   verifying the pain is associated with regions innervated by at least one of the patient's occipital nerves so as to identify a targeted region of at least one occipital nerve;
   positioning a flexible, coiled neurostimulation lead having a single electrode proximate to, but not in direct physical contact with, the targeted region;
   delivering preliminary therapy for a period of time via the lead while simultaneously preventing migration of the lead, the preliminary therapy comprising pulsed electrical signals sufficient to activate the occipital nerve to provide pain relief while avoiding activation of non-target type III and IV nerve fibers within the occipital nerve due to the single electrode being proximate to but not in physical contact with the targeted region; and
   removing the lead after the patient reports a reduction in pain.

2. The method of claim 1, further comprising:
   monitoring the pain reported by the patient subsequent to the preliminary therapy;
   upon a report from the patient of pain that is similar to the preliminary therapy, providing a surgically implanted system comprising a second flexible, coiled neurostimulation lead positioned proximate to, but not in direct contact with, the targeted region and a subcutaneous electrical stimulation device located proximate to one of the patient's upper chest, clavicle, skull and neck;
   connecting the second lead to the electrical stimulation device and subcutaneously fixing the electrical stimulation device within the patient; and
   delivering long term therapy via the second lead and the electrical stimulation device.

3. The method according to claim 2, wherein the electrical stimulation device is attached to the patient's fascia.

4. The method according to claim 1, wherein the preventing migration of the lead comprises allowing tissue ingrowth within the lead.

5. A method for treating pain in a patient, the method comprising:
   verifying the pain is associated with regions innervated by at least one of the patient's occipital nerves so as to identify a targeted region of at least one occipital nerve;
   positioning a flexible, coiled neurostimulation lead having a single electrode proximate to, but not in direct physical contact with, the targeted region;
   surgically implanting a subcutaneous electrical stimulation device proximate to one of the patient's upper chest, clavicle, skull and neck;
   connecting the lead to the electrical stimulation device in parallel;

subcutaneously fixing the electrical stimulation device within the patient; and delivering neurostimulation therapy via the electrode while simultaneously preventing migration of the lead, the therapy comprising pulsed electrical signals sufficient to activate the occipital nerve to provide pain relief while avoiding activation of non-target type III and IV nerve fibers within the occipital nerve due to the single electrode being proximate to but not in physical contact with the targeted region.

6. The method according to claim 5, wherein the electrical stimulation device is attached to the patient's fascia.

7. A method for treating pain in a patient, the method comprising:

verifying the pain is associated with regions innervated by at least one of the patient's occipital nerves so as to identify a targeted region of at least one occipital nerve;

positioning a flexible, coiled neurostimulation lead having a single electrode proximate to and spaced a distance from, but not in direct physical contact with, the targeted region; and delivering therapy for a period of time via the lead while simultaneously preventing migration of the lead, the therapy comprising pulsed electrical signals sufficient to activate the occipital nerve to provide pain relief without stimulating muscle contractions and sensations of discomfort, wherein the pulsed signals are directionally transmitted only to the targeted region while simultaneously preventing the pulsed signals from stimulating non-targeted type III and IV nerve fibers due to the single electrode being spaced the distance from the targeted region.

8. The method according to claim 7, further comprising providing a plurality of leads and positioning each lead so that each lead is operatively associated with a plurality of targeted regions, said plurality of targeted regions in each located in separate occipital nerves.

9. The method according to claim 7, wherein the targeted region comprises first and second areas; wherein the electrode includes a length of exposed conductive wires, said length having a first exposed end and a second opposed end with a middle length situated therebetween; and further comprising positioning the first exposed end proximate to and spaced a first exposed distance from, but not in direct physical contact with, the first area and the second exposed end proximate to and spaced a second exposed distance from, but not in direct physical contact with, the second area.

10. The method according to claim 9, wherein the pulsed signals are adjusted so that appropriate levels of therapeutic current are delivered at the first and second exposed ends while current delivered by the middle length does not stimulate muscle contractions and sensations of discomfort.

11. The method according to claim 9, wherein the first area is located on a first occipital nerve and the second area is located on a second occipital nerve.

12. The method according to claim 11, wherein the lead is substantially parallel to a transverse plane.

13. The method according to claim 11, wherein the lead is substantially parallel to at least one of a sagittal plane and a coronal plane.

14. The method according to claim 7, wherein the conductive members are arranged to create a plurality of coils in the lead.

15. The method according to claim 7, wherein the preventing migration of the lead comprises allowing tissue ingrowth within the lead.

* * * * *